United States Patent [19]
Maeshima et al.

[11] Patent Number: 6,108,079
[45] Date of Patent: Aug. 22, 2000

[54] METHOD FOR MEASURING CRYSTAL DEFECT AND EQUIPMENT USING THE SAME

[75] Inventors: Muneo Maeshima, Mito; Kazuo Takeda, Tokorozawa; Isao Nemoto, Hitachinaka; Shigeru Matsui, Hitachinaka; Yoshitaka Kodama, Hitachinaka, all of Japan

[73] Assignee: Hitachi, Ltd., Tokyo, Japan

[21] Appl. No.: 09/245,195

[22] Filed: Feb. 5, 1999

[30] Foreign Application Priority Data

Feb. 6, 1998 [JP] Japan ................................ 10-026134

[51] Int. Cl.⁷ .......................... G01N 21/00; G01N 21/86
[52] U.S. Cl. .................. 356/237.2; 250/559.33; 250/559.45; 356/375
[58] Field of Search .................. 250/559.38, 559.45, 250/559.3, 559.29; 356/375, 237.1, 237.2, 237.3–237.5

[56] References Cited

U.S. PATENT DOCUMENTS

| | | | |
|---|---|---|---|
| 4,988,886 | 1/1991 | Palum et al. | 356/561 |
| 5,247,186 | 9/1993 | Toda | 250/561 |
| 5,621,218 | 4/1997 | Tanaka | 250/559.34 |
| 5,801,835 | 9/1998 | Mizutani et al. | 356/375 |
| 5,903,342 | 5/1999 | Yatsugake et al. | 356/237.4 |
| 5,936,726 | 8/1999 | Takeda et al. | 356/237.2 |

FOREIGN PATENT DOCUMENTS

| | | |
|---|---|---|
| 8-75980 | 3/1996 | Japan . |
| 8-96738 | 4/1996 | Japan . |

OTHER PUBLICATIONS

"A New Measurement Method of Micro Defects Near the Surface of Si Wafers; Optical Shallow Defect Analyzer (OSDA)" in Mat. Res. Soc. Symp. Proc. vol. 442 1997 Materials Research Society, pp. 37–42.

*Primary Examiner*—Frank G. Font
*Assistant Examiner*—Layla G. Lauchman
*Attorney, Agent, or Firm*—Kenyon & Kenyon

[57] ABSTRACT

In order to measure an inner defect of a sample with a certain high accuracy even if the sample surface of the moved up and down by flatness irregularity of the sample and problem on accuracy of the sample movement stage, incident light beams having two wavelength and respective different penetration depths for the sample are slantingly irradiated on the surface of the moving sample 15 from irradiation optical systems 4, 8, and the inner defect of the sample is measured by detecting the scattering light occurred from the interior of the sample with a detection optical system 9 arranged over the sample surface. A distance measurement means 14 is located in an upstream of a movement direction of said sample than said irradiation optical system 4, 8 and said detection optical system 9, thereby a surface height of said sample is measured. When a measured point on sample measured by the distance measurement means 14 is arrived at a lower part of the detection optical system 9, height positions of the irradiation optical system and the detection optical system are controlled by piezo electric elements 11,12,13 so that the irradiation optical system and the detection optical system are located at predetermined positions relating to the measured point.

12 Claims, 3 Drawing Sheets

METHOD FOR MEASURING CRYSTAL DEFECT AND EQUIPMENT USING THE SAME

BACKGROUND OF THE INVENTION

Present invention relates to an analysis equipment of sample, more in detail, relates to a crystal defect measurement method and equipment using the same for measuring crystal defect such as sludge or stacking fault in a semiconductor wafer, especially a silicon wafer.

According to the improvement of integration degree of large scale integrated circuit (LSI), degradation of non-defective unit acquisition rate and reliability caused by failure of the metal oxide semiconductor (MOS) transistor which constitutes the large scale integrated circuit, becomes a big problem recently.

As possible cause of failure of metal oxide semiconductor transistor, breakdown of a gate oxide junction and leak electric current in a connected part are typical. Most of the failure of these metal oxide semiconductor transistor are originated in crystal defect in a silicon substrate.

That is, in the large scale integrated circuit manufacturing process, when the crystal defect exists in a near surface region of the silicon substrate converted into the silicon oxide by oxidation, construction defect is formed in a silicon oxide layer, and the breakdown occurs in the large scale integrated circuit operation.

Moreover, leak current occurs abundantly when the crystal defect exists in a depletion layer of the connection part.

When the crystal defect is formed in the near surface region where element is formed in silicon substrate, and it is not desirable, because failure of metal oxide semiconductor transistor occurs, and in this way, the defect measurement is important in a quality control of silicon single crystal.

As conventional method to measure such a defect, there is a method mentioned in Mat. Res. Soc. Symp. Proc. Vol. 442 1997 Materials Research Society, pages 37 to 42.

In this reference, a method is shown in which two light beams having different wavelength which penetration depth thereof for a silicon wafer are different three times or more each other, are irradiated slantingly on the sample surface by a slantingly incident optical system, and a scattering light from a crystal defect is detected on a vertical direction of a surface of said sample.

According to this method, the depth of the crystal defect can be known from a ratio of a scattering light intensity of a short wavelength and a scattering light intensity of a long wavelength, and size of the crystal defect can be known from the scattering light intensity of the long wavelength.

In this way according to the measurement method adopting the slantingly incident optical system, when the light beam diameter to be irradiated is squeezed to be small, irradiation position of the light beam moves up and down according to flatness irregularity of the wafer and problem on accuracy of the sample movement stage.

Because of this moving up and down, the irradiation position of the slantingly incident light beam is moved on the sample surface to a direction parallel to the sample surface.

When the irradiation beam is irradiated with an angle Brewster angle of silicon (75°) and the surface height of the wafer is moved 0.5 $\mu$m as stated above, the beam irradiation position moves about 1.9 $\mu$m on the wafer surface. Moreover because of the moving up and down identically, detection position of the detection system changes up and down, and an accurate scattering light signal strength is not provided.

Therefore, it becomes important that a relative position of a beam irradiation region and a detection region is kept to be constant, and a distance of them from the sample is kept to be constant.

As an example of the control system of the irradiation or detection system, Japanese Patent Laid-open No. 8-75980 bulletin is published.

In this bulletin, for an object of image observation, an objective lens or a sample stage of an optics type microscope is moved up and down so as to make the contrast high. In an irradiation optical system (lighting object), a uniform lighting is suitable in order to observe the image with a high contrast, when it is irradiated through an objective lens or when it is irradiated from a bottom of the sample stage, and there is no need to pay any special attention.

On the other hand, in the crystal defect analysis equipment, a spot diameter of the irradiation light is enough smaller than a visual field of the objective lens, and moreover because irradiation light is slantingly incident, the irradiation position on the sample surface is changed according to up and down drift of the sample surface.

Therefore, the irradiation system needs to be controlled precisely.

There is a technique shown in Japanese Patent Laid-open No. 8-96738 bulletins as an example of a focal point matching system of a scan type electron microscope.

That is, a probe light source for the focal point matching is provided, and a gravity position of a reflected light from the sample surface is detected by a position sensor, the focal point position is changed by changing an exciting current value of the objective lens.

In the crystal defect measurement equipment, it is equivalent for aligning only the irradiation system, it is different from controlling the objective lens of the detection system.

SUMMARY OF THE INVENTION

The control of the irradiation or the detection system or the focal point matching in prior art as stated above is performed for an image observation, an object of the focal point matching is to raise contrast of the image and the sample stage stops during image observation (measurement), and only the control of the irradiation system or detection system is performed.

On the other hand, because the crystal defect measurement equipment is used for calculating a defect depth from the sample surface.

The standard where optical system is aligned is a sample surface, and the optical system is not limited to be aligned in order to raise the contrast of the image.

Moreover, the focal point matching is need to do while the stage is moving (during measurement) by real time, and both of an irradiation system and a detection system are needed to be controlled in order to measure scattering light intensity.

Accordingly crystal defect measurement equipment cannot be applied a method in the prior art.

Moreover, when a focal point matching method to make light such as semiconductor laser incident from a detection system arranged on a direction perpendicular to the sample to a neighborhood of a measurement region of the sample, or a focal point matching method to make the light slantingly incident to the neighborhood of the measurement region of the sample is applied to the crystal defect measurement equipment, there arise following problems.

In the first, for the crystal defect analysis equipment using two wavelength which penetration depth thereof are different three times or more each other, the light to be irradiated for focal point matching becomes a noise when measuring the scattering light intensity from the defect accurately.

Even if, the wavelength of the light used to match focus is different greatly from one of the two wavelengths used for detecting the defect, possibility to approach to the other of the two wavelengths is high.

In the second, during the sample measurement (during scan), the sample movement system (r-θ stage) is always rotated and does a translation, and the optical system or the stage movement system should be selected to have a proper response speed.

In the third, in a case a particle of a big particle size exists on the silicon wafer surface as the sample, for example, if a technique in prior art is taken, for the purpose of an image observation, the focal point matches to the position where contrast or signal from the image becomes big namely, that is, a position of the particle exists.

In the crystal defect measurement equipment, the object of the focal point matching is not in observing the image with a high-resolution, but in keeping a relative position relationship of the irradiation region of the irradiation light and the observation region of the detection system, uniform, thereby, as the focus fits to the big particle, degradation of the measurement sensitivity is caused as a problem.

In the fourth, as making the light slantingly incident, focus of the irradiation system needs to be controlled so as to be matched, and detection system needs to be controlled too in order to measure the scattering light intensity signal with a good accuracy, therefore, control system for the focal point matching becomes complicated.

The present invention is provided referring to these problems in the prior art, and in a crystal defect measurement method for measuring an inner defect of sample, by letting light beams having two wavelengths come in slantingly to a surface of the sample, and by detecting scattering lights generated from interior defects of said sample on a direction perpendicular to said surface, even if it is assumed that the sample surface changes up and down because of flatness irregularity of the sample and problem on accuracy of a sample movement stage, the object of the present invention is to provided a method and an equipment to be able to measure an inner defect of the sample always with a constant accuracy, and to check the particle stuck on the sample surface.

In the present invention, height positions of an irradiation optical system and a detection optical system for the sample surface is capable to be adjusted with piezo electric elements, and a length measurement sensor is arranged to a position where a certain point on the sample arrives earlier than an irradiation region of the irradiation light and an observation region of the detection system relating to a movement direction of the sample.

Here, as the length measurement sensor, a sensor of a electrostatic capacitance type is used which has a probe having a fully larger diameter than a particle size of a big particle, thereby a focal point matching function is prevented from reacting excessively by the particle.

The output from the length measurement sensor is input into a controller of the piezo electric elements, the piezo electric elements are expanded and contracted up and down direction only an amount corresponding to a quantity of displacement of the sample surface, and the above object is achieved by controlling a position relationship between the irradiation region of the irradiation light and the detection region of the scattering light so as to keep constant relatively.

That is, as a method in the present invention, in a crystal defect measurement method for measuring an inner defect of sample, by letting light beams come in slantingly from an irradiation optical system to a surface of the sample being moved, said light beams having two wavelengths and penetration depth thereof to the sample being different, and by detecting scattering lights having said two wavelengths generated from interior of said sample with an detection optical system arranged upward of said surface, the method in the present invention is characterized by comprising a step for measuring a height of said surface with a distance measurement means of an electrostatic capacitance type arranged to an upstream of a moving direction of the sample than said irradiation optical system and said detection optical system, and a step for controlling a height position of said irradiation optical system and said detection optical system to said sample, so that said irradiation optical system and said detection optical system are disposed to a predetermined position for said measuring point, when a measuring point on said sample measured by said distance measurement means arrives at lower part of said detection optical system.

Here it is desirable for the penetration depth into the sample of the light beams having two wavelength to be different three times or more.

As an apparatus in the present invention, in a crystal defect measurement equipment for measuring an inner defect of sample, comprising a sample movement system to let sample move, an irradiation optical system for irradiating light beams slantingly to a surface of the sample being moved, said light beams having two wavelengths and penetration depth thereof to the sample being different, and an detection optical system arranged upward of said surface, wherein an inner defect of said sample is measured by detecting scattering light having two wavelengths from sample interior with said detection optical system, the apparatus in the present invention comprises a distance measurement system for measuring a surface height of said sample being moved, and an optical system movement system for moving said irradiation optical system and said detection optical system to a direction that is perpendicularity to said surface, and a control system for controlling said optical system movement system, and the apparatus in the present invention is characterized in that said control system controls said optical system movement system so as to make a distance between said surface of said sample, and said irradiation optical system and said detection optical system, a predetermined value based on said surface height of said sample measured by said distance measurement system.

Here, it is desirable for the penetration depth into the sample of the light beams having two wavelength to be different three times or more. The distance measurement system has a distance measurement device of electrostatic capacitance type.

Moreover, the distance measurement system may have plural distance measurement devices of electrostatic capacitance type.

The irradiation optical system and the detection optical system are unified constitutionally, and optical system movement system may be a unified one of the irradiation optical system and the detection optical system that is moved by the piezo electric element.

Moreover the irradiation optical system and the detection optical system may be moved separately, and the optical system movement system may have a piezo electric element for making the irradiation optical system move and a piezo electric element for making the detection optical system move.

As an apparatus in the present invention, in a crystal defect measurement equipment for measuring an inner defect of sample, comprising a sample movement system to let sample move, an irradiation optical system for irradiating light beams slantingly to a surface of the sample being moved, said light beams having two wavelengths and penetration depth thereof to the sample being different, and an detection optical system arranged upward of said surface, wherein an inner defect of said sample is measured by detecting scattering light having two wavelengths scattered from sample interior with said detection optical system, said crystal defect measurement equipment being characterized by said sample movement system rotating said sample and moving a rotation center of said sample simultaneously so as to make a linear velocity at an irradiation position by said irradiation optical system constant, and further comprising a distance measurement system being located in an upstream of a movement direction of said sample than said irradiation optical system and said detection optical system for measuring a surface height of said sample being moved, a storage system for storing said surface height of said sample measured by said distance measurement system, and an optical system movement system for moving said irradiation optical system and said detection optical system to a direction that is perpendicularity to said surface, and a control system for controlling said optical system movement system, wherein said control system controls said optical system movement system so as to make a distance between said surface of said sample, and said irradiation optical system and said detection optical system, a predetermined value based on said surface height of said sample measured by said distance measurement system.

Here, it is desirable for the penetration depth into the sample of the light beams having two wavelength to be different three times or more.

The above mentioned control system in the present invention reads out the surface height of the measurement point memorized in a storage device system when a measurement point where measurement of the surface height is performed by the distance measurement system arrives at the lower part of the detection optical system, and can control the optical system movement system so that a distance between the surface of the sample and the irradiation optical system and the detection optical system becomes to be a predetermined value. Furthermore, in the present invention, a time delay system to delay output of said distance measurement system only a time necessary for the measurement point where the surface height thereof is measured by the distance measurement system to arrive at a position just under the detection optical system, is provided in stead of said storage system, wherein said control system controls said optical system movement system so as to make a distance between said surface of said sample, and said irradiation optical system and said detection optical system to be a predetermined value, based on information of the surface height delayed by said time delay system.

In present invention, the light is not used as a probe for a focal point matching a probe light for the focal point matching does not overlap to the scattering light signal from the crystal defect as the noise.

Moreover, because the present invention does not relates to a focal point matching method to make the contrast the maximum, focus does not fit the particle which stuck to the sample surface.

According to the present invention, as the measurement is performed in a condition as that the position relationship of the irradiation optical system and the sample surface, and the detection optical system and the sample surface are always constant, the measurement of the inner defect of the single crystal can be always done with a constant high accuracy.

DETAILED DESCRIPTION OF THE PREFERRED EMBODIMENTS

Referring to the drawings, and form of the embodiments of the present invention will be explained as follows.

Figure 1:
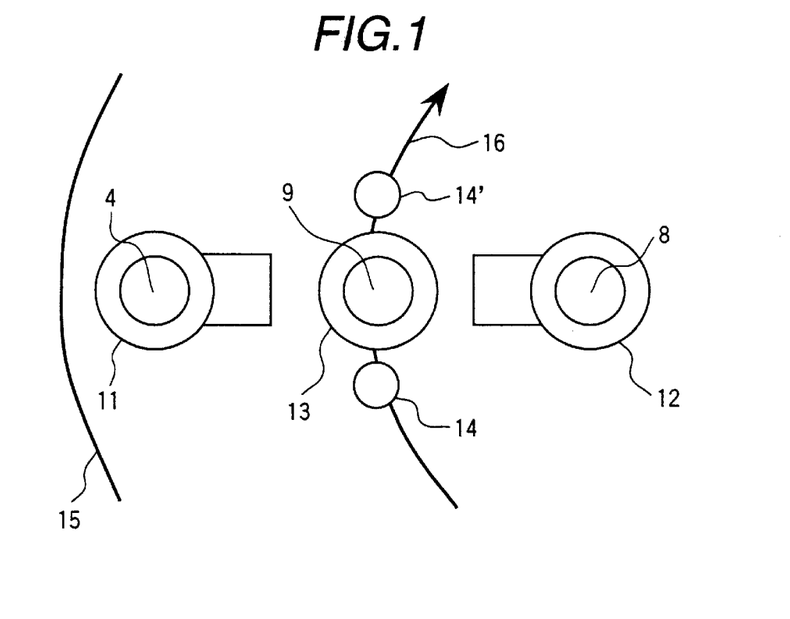
FIG. 1 shows a top-view of a schematic diagram of a irradiation and detection optical system of a crystal defect measurement equipment in the present invention.
Figure 2:
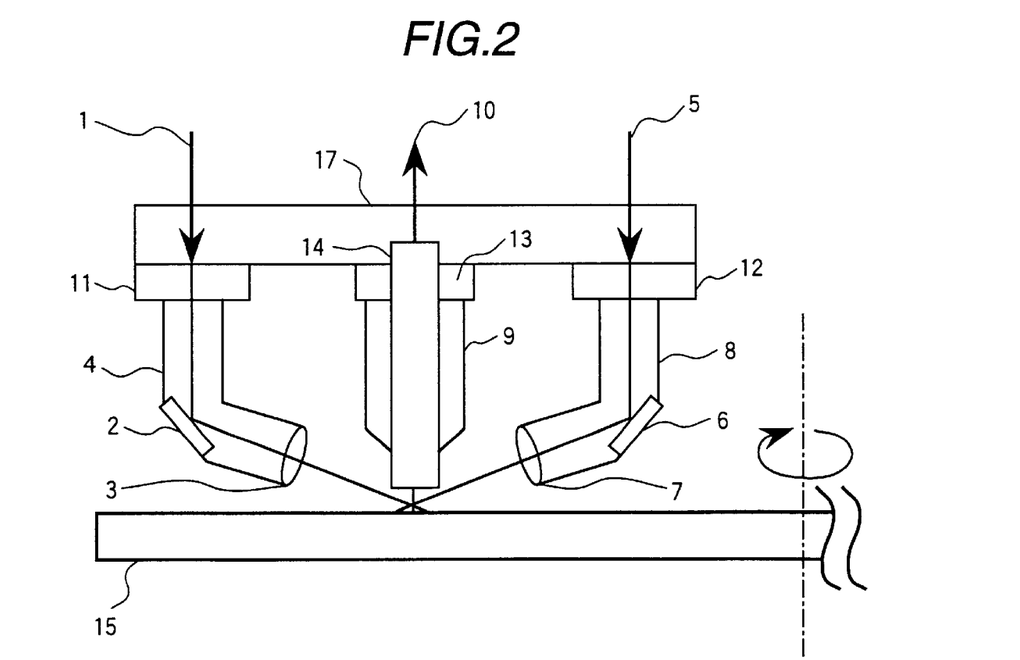
FIG. 2 shows a side-view of a schematic diagram of a irradiation and detection optical system of a crystal defect measurement equipment in the present invention.

A general description of an irradiation and detection optical system of a crystal defect measurement equipment according to the present invention will be shown in FIG. 1 and FIG. 2.

FIG. 1 is a top-view that shows position relationship of the irradiation and detection optical system, and FIG. 2 is a side view.

Here, the detection optical system for detecting an inner defect of a silicon wafer will be explained for an example.

In a minute irradiation region on a sample, namely silicon wafer 15, a first irradiation light 1 is irradiated from a first irradiation system 4, and a second irradiation light 5 is irradiated from a second irradiation system 8.

The silicon wafer 15 is held on a sample stage so as to be moved, and the inner defect of the wafer is detected continually by scanning the irradiation region of the silicon wafer 15 continually.

A scattering light from the inner portion of the silicon wafer 15 is detected through an objective lens 9.

As explained in detail later, distance to a measuring point is measured by a length measuring sensor 14, before the measuring point of the silicon wafer 15 enters the irradiation region, and the first and the second irradiation systems 4, 8 are controlled so that the distance between the first irradiation systems 4 and the objective lens 9 or the second irradiation systems 8 and the objective lens 9 becomes to be a predetermined distance, when the measuring point entered the irradiation region.

As the first irradiation light 1, a second harmonic wave light of YAG laser of a wavelength 532 nm is used, said second harmonic wave light being obtained by adjusting a polarized light direction to a surface of the silicon wafer 15 to be in p-polarized light with a polarizer.

The first irradiation light 1 is reflected by a reflection mirror 2, is condensed with a first condenser lens 3, and is irradiated on the surface of the silicon wafer 15 from a direction where an optical axis of an incident light of the first irradiation light 1 becomes Brewster angle of silicon (about 75 degrees).

The p-polarized light is irradiated by Brewster angle, and the reflection at the silicon surface is reduced, thereby loss of the irradiation light intensity to the inner defect is reduced.

It needs not to always be irradiated with this condition, however it is preferable to be irradiated with this condition.

A light having a wavelength 810 nm provided from a semiconductor laser is used as the second irradiation light 5, the second irradiation light 5 is reflected by a reflection mirror 6, is condensed with a second condenser lens 7, and is irradiated on the surface of the silicon wafer 15 from a direction where an optical axis of an incident light of the second irradiation light 5 becomes Brewster angle of the silicon (about 75 degrees).

As wavelengths of the first irradiation light 1 and the second irradiation light 5, different two wavelengths are selected in which penetration depth to the silicon wafer 15 of one of the two wavelengths is three times or more than that of the other.

Because, when one of the penetration depth s is different three times or more than the other, attenuation of the light having a long wavelength becomes about 50% in a depth region that a short wavelength may immerse, and when calculating a particle size of the scattering body from a scattering light signal of the long wavelength according to Rayleigh scattering theory, the error is estimated to be less than 10%. Moreover, when using the first irradiation light 1 and the second irradiation light 5, in order to make an affection of the scattering light (HAZE) by micro-roughness of the surface of the silicon wafer 15 small, and to make detectivity of the crystal defect improved, they are narrowed down to thin beam of a diameter of 5–10 μm extent, and are irradiated on the surface of the silicon wafer 15.

For example, when the beam diameters of the irradiation lights 1, 5 are provided to be about 5 82 m, on the surface of silicon wafer 15, a beam spot of ovals of a longer axis 5 μm and breadth 20 μm or so, is formed.

The irradiation light penetrates the silicon wafer 15 through the beam spot, and the inner defect in the region of the depth about 0.5 μm may be measured.

The incident lights having two wavelengths coming in the silicon wafer 15 from the first and second irradiation systems 4, 8, are scattered when reaching the inner defects of the silicon wafer.

The forward scattering light among the scattered lights does not come back to outside of the wafer again.

Scattering light of a bigger angle than a critical angle (about 14.5 degrees) by a boundary surface between the silicon and the air among the back scattering light, is totally reflected inside and at the surface of the silicon wafer 15, thereby does not arrive at outside of the wafer.

Only scattering light scattered with the angle smaller than the critical angle, passes through the critical angle of the silicon wafer 15 and arrives at the outside of the wafer. The scattering light which arrived at the outside of the wafer, is caught by the objective lens 9, and goes to a sensor as the scattering light 10.

A principle for measuring the inner defect by using thee scattering lights having two wavelengths will be explained in the next.

When a refraction index in a wavelength λ of the silicon is n and extinction coefficient is k, the penetration depth $\lceil$ that amplitude of the incident light becomes 1/e of a value at the surface is given by a following equation 1.

$$\lceil = \lambda / 2 \pi k \quad (1)$$

Accordingly, the irradiation light intensity that comes into the sample (a silicon wafer) with an incident angle of θ from the air, becomes to converge a value obtained by $\exp[(-2Z/\lceil)\cos[\arcsin(\sin\theta/n)]]$ than the surface, at a portion of the depth Z from the surface, referring to the refraction index in the silicon given by arcsin(sin θ/n).

Then, as an example for a case, the light is irradiated with an incidence angle θ on the sample surface from the air, and the irradiated light scattered by the defect of the sample interior to a sample surface direction is detected with a certain solid angle.

When an integral scattering cross section of the defect about the detection solid angle is defined as σ, irradiation light intensity is I, a transmission factor of the irradiated light in the incidence angle on a wafer surface is Ti, and the transmission factor from the wafer inside to the air of the scattered light is Ts, Scattering light intensity S from the defect which is in a position of a depth Z than the wafer surface referring to both of attenuation of the irradiation light and attenuation of the scattering light is obtained as follows;

$$S = Ti \cdot Ts \cdot I \cdot \sigma \cdot \exp[-(2Z/\lceil)[1+1/\cos(\arcsin(\sin\theta/n))]] \quad (2)$$

When refraction indexes of the sample to wavelengths λ1 and λ2 are respectively defined as n1, n2 penetration depth respectively $\lceil 1$, $\lceil 2$, irradiation light intensitys respectively I1, I2, scattering light intensitys that are measured respectively S1, S2, integral scattering cross sections respectively σ1, σ2, irradiated light transmission rates respectively Ti1, Ti2, scattering light transmission rates respectively Ts1, Ts2, equations (3) and (4) are obtained as follows;

$$S_1 = Ti_1 \cdot Ts_1 \cdot I_1 \cdot \sigma_1 \cdot \exp[-(2Z/\lceil_1)[1+1/\cos(\arcsin(\sin\theta/n_1))]] \quad (3)$$

$$S_2 = Ti_2 \cdot Ts_2 \cdot I_2 \cdot \sigma_2 \cdot \exp[-(2Z/\lceil_2)[1+1/\cos(\arcsin(\sin\theta/n_2))]] \quad (4)$$

Here $\lceil_1 < \lceil_2$.

From equations (3) and (4), equation (5) is obtained as follows;

$$Z = C_1 \cdot \ln[C(S_2/S_1)(\sigma_1/\sigma_2)] \quad (5)$$

Here, $C_1$ and $C_2$ are optics fixed number and an equipment fixed number of the sample and are defined as follows;

$$C_1 = 1/[(2/\lceil_1)(1+1/[\cos(\arcsin(\sin\theta/n_1))])-(2/\lceil_2)(1+1/[\cos(\arcsin(\sin\theta/n_2))])] \quad (6)$$

$$C2 = (I_1/I_2)(Ti_1 \cdot Ts_1/Ti_2 \cdot Ts_2) \quad (7)$$

As Cl and $C_2$ are the equipment fixed numbers, if $(S2/S_1)(\sigma_1/\sigma_2)$ is offered, Z is may be obtained.

Here $(S_2/S_1)$ is a ratio of the signal strength and is obtained from a measured value.

Furthermore, if the defect size (d) is fully small than an irradiation wavelength, and it is within Rayleigh scattering region (less than particle size 0.2 μm as a rule of thumb), a relationship of $\sigma \propto d^{-6}\lambda^{-4}$ is obtained about each wavelength and further, a relationship of $\sigma_1/\sigma_2 = (\lambda_2/\lambda_1)^{-4}$ is provided.

By adding this condition to the equation (5), following equation (8) is provided.

$$Z = C_3 \cdot \ln(S_2/S_1) + C4 \quad (8)$$

However, $C_3$ and $C_4$ are the equipment fixed numbers that do not depend on the defect, too.

As stated above, the depth Z of the defect is obtained from the scattering light intensity S1 of the wavelength λ1 and the scattering light intensity $S_2$ in wavelength $\lambda_2$. In next, relating to the defect detected with the wavelength $\lambda_1$ of the light having a bigger absorption coefficient, the particle size d of the defect is obtained by using the scattering light intensity $S_2$ in the small wavelength $\lambda_2$ of the light having a smaller absorption coefficient by a equation (9) as follows.

$$Ln(d)=(1/6)ln(S_2)+C_5 \qquad (9)$$

Here, numeral $C_5$ is a equipment fixed number that does not depend on defect. However, in the equation (9), relating to the penetration depth $\lceil_1$ of the wavelength $\lambda_1$ and the penetration depth $\lceil_2$ of the wavelength $\lambda_2$, a condition of $\lceil_1 << \lceil_2$ is needed. Under this condition, the equation (9) is derived as follows.

That is, relating to the defect to be satisfied with the condition of $Z<\lceil_1<<\lceil_2$, a relation of $Z/\lceil_2 \approx$zero is obtained based on the equation (4), and an equipment fixed number C6 that does not depend on the defect is obtained as $S_2=C_6\sigma_2$.

Besides, in Rayleigh scattering region, as a condition of $\sigma 2\ d^{-6}$ exists, the equation (9) is obtained.

In this way, by detecting the scattering light intensity $S_1$ of the wavelength $\lambda_1$ and the scattering light intensity S2 in wavelength $\lambda_2$, the depth Z of the inner defect may be obtained by the equation (8), and the size of the inner defect may be obtained by the equation (9).

In FIG. 1, the first irradiation system 4 to irradiate the first irradiation light 1 having the wavelength $\lambda_1$, the second irradiation system 8 to irradiate the second irradiation light 5 having the wavelength $\lambda_2$, and the objective lens 9 are respectively fixed on a common optical system holder 17 through the first to the third piezo electric element 11 to 13.

Here, the first irradiation system 4, the second irradiation system 8 and the objective lens 9 are unified and they may be driven with one piezo electric element.

However, as the weight of each irradiation system and the detection system becomes big, the load of the piezo electric element becomes big, moreover a responsibility thereof falls too, it is preferable to drive with separated three piezo electric element.

Here, direction of the telescopic motion of the piezo electric element (the stroke direction) is vertical on the surface of the silicon wafer.

In this place, the first and second irradiation systems 4, 8, and the objective lens 9 are provided independently, control method of the respective piezo electric element having movable range of 100 $\mu$m extent will be explained. Position control with the piezo electric element utilizes a telescopic motion of the element, and there is not a rotational moving element comparing with a method by using a motor. Therefore, it has a merit that foreign substance caused by the moving of the element does not arise, when arranging on the wafer surface.

Moreover, there is advantage too that a minute position control less than 0.1 $\mu$m is easy.

In measuring the defect, the silicon wafer 15 as the sample moves to a direction shown by an arrow 16 in FIG. 1.

That is, the length measuring sensor 14 is disposed to upstream of the irradiation system and the detection system, the measuring point on the sample 15 passes just under the length measuring sensor 14 before passing through the irradiation region of the irradiation light and the detection region of the detection system, and the distance from the optical system holder 17 may be measured.

Plurality of the length measuring sensors may be provided.

For example, the second length measuring sensor 14' is positioned to be symmetric for the objective lens 9, Mean value of the distance measured with two length measuring machine sensor 14,14' may be reflected as a distance between the objective lens 9 and the silicon wafer 15.

By arranging in this way, even if it is assumed that the measurement error occurred, caused by the difference of detection timing between the length measuring sensor and the irradiation system, this error can be restrained easily.

Moreover, when, the silicon wafer is scanned in a spiral state, the distance of the measuring point from the silicon wafer is different according to a difference of rotational radii in a periphery and internal circumferences of the wafer.

For this reason, in the case that the length measuring sensor is disposed only in a position of the length measuring sensor 14,the length measuring sensor can not be always disposed in the upstream of the irradiation system and the detection system.

Then, the place where two length measuring sensors are installed, is not on a moving path of the measuring point as shown in FIG. 1, but may be disposed on a neighborhood of the first irradiation system 4 and the second irradiation system 8 so that a line to tie the two length measuring sensors intersects with the sample moving direction 16.

The output from plural length measuring machine sensors may be distributed (proportional distribution) according to a distance from a measured wafer center (rotational radius of the measuring point).

Total scanning with the irradiation light for the silicon wafer is performed in spiral state by rotating the silicon wafer and by moving a center of the wafer simultaneously.

In this scanning, when an angular velocity of the rotation is done with $\omega$ and the distance from the rotational center of the measuring point is r, the total scanning is controlled so as to make $r \times \omega$ always constant, that is, to make a linear velocity constant.

In a moment when the scattering body passes through the irradiation region, a scattering light like a pulse occurs. As the scattering body, there are crystal defect such as oxygen sludge (SiO two child) or transposition contained in the sample (the silicon wafer) 15 and the foreign substances stuck to the wafer surface.

A distance sensor of electrostatic capacitance type of a sensor diameter of 5 mm and of detection distance limit of ±250 $\mu$m extent is used as the length measuring sensor 14, thereby comparing the focal point matching method using a light as the probe, it becomes easy to avoid a probe light for distance measurement from overlapping as noise to the pulse scattering light signal.

Moreover, comparing with the focal point matching method improved contrast thereof, it become easy to avoid to fit focus on the upper surface of the foreign substance having a big particle size stuck on the wafer surface.

The length measuring sensor 14 passes over the sample earlier than the irradiation region and the detection region for measuring the scattering light, and the sample is scanned with a constant angular velocity.

The time of the measuring point after passing under the center of the length measuring sensor 14 till arriving just under the objective lens 9 always becomes constant.

By making the output of the length measuring sensor 14 delay as this constant time, and making the position of the first to third piezo electric element 11 to 13 moved up and down, the distance between the irradiation system 4, 8 and the sample 15 and the distance between the detection system 9 and the sample 15 are controlled so as to be constant.

Moreover, after the output of the length measuring sensor 14 is stored in a memory device, the output stored in a memory device may be read out so as to control the piezo electric element 11 to 13 on a timing when the measuring point on the sample which measured distance by the length measuring sensor 14 passes the center of the objective lens 9.

In addition to above in this embodiment of the present invention, in order to control the distance between the irradiation system or the detection system and the sample surface to be constant, the irradiation system and the detection system are moved up and down, however the present invention is not limited to this system.

For example, it is possible to control the stage mounting the silicon wafer up and down.

Figure 3:
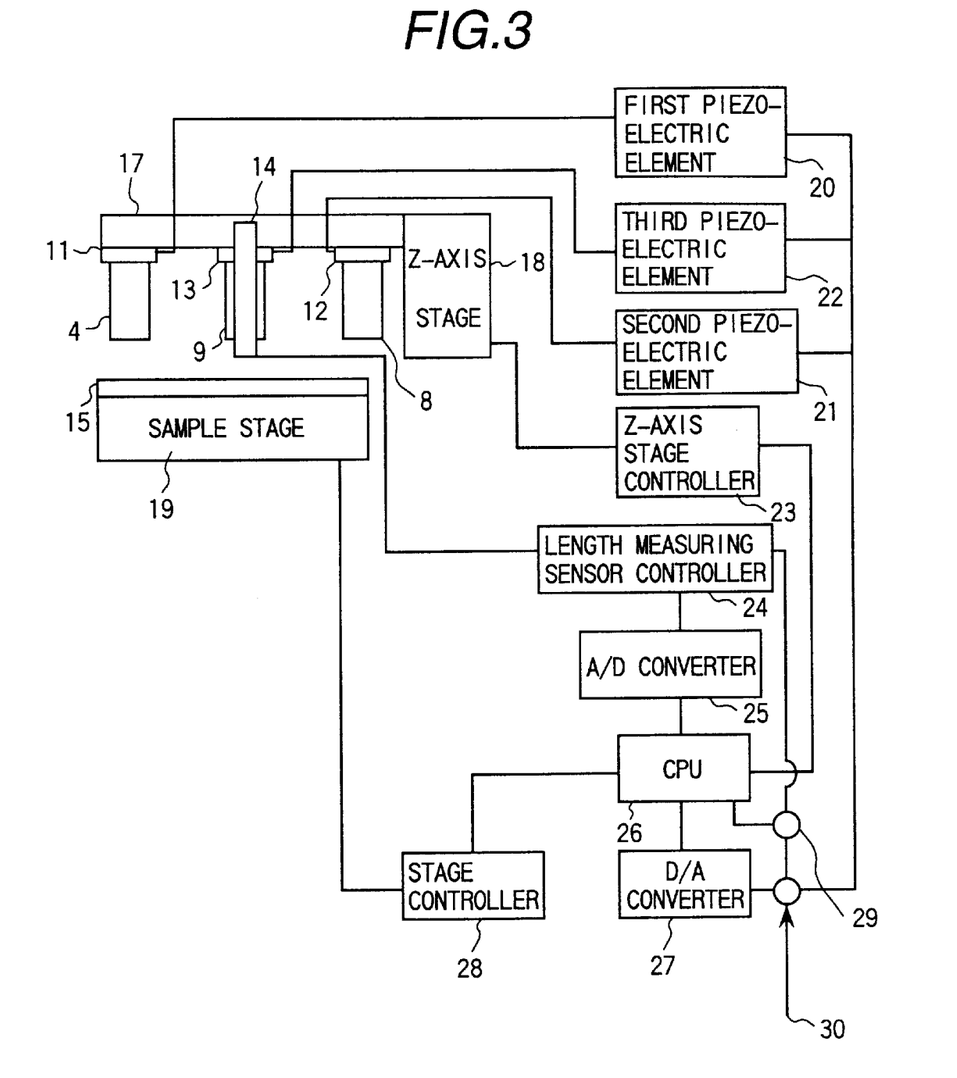
FIG. 3 shows a block diagram which represents a control system for matching a focal point.
Figure 4:
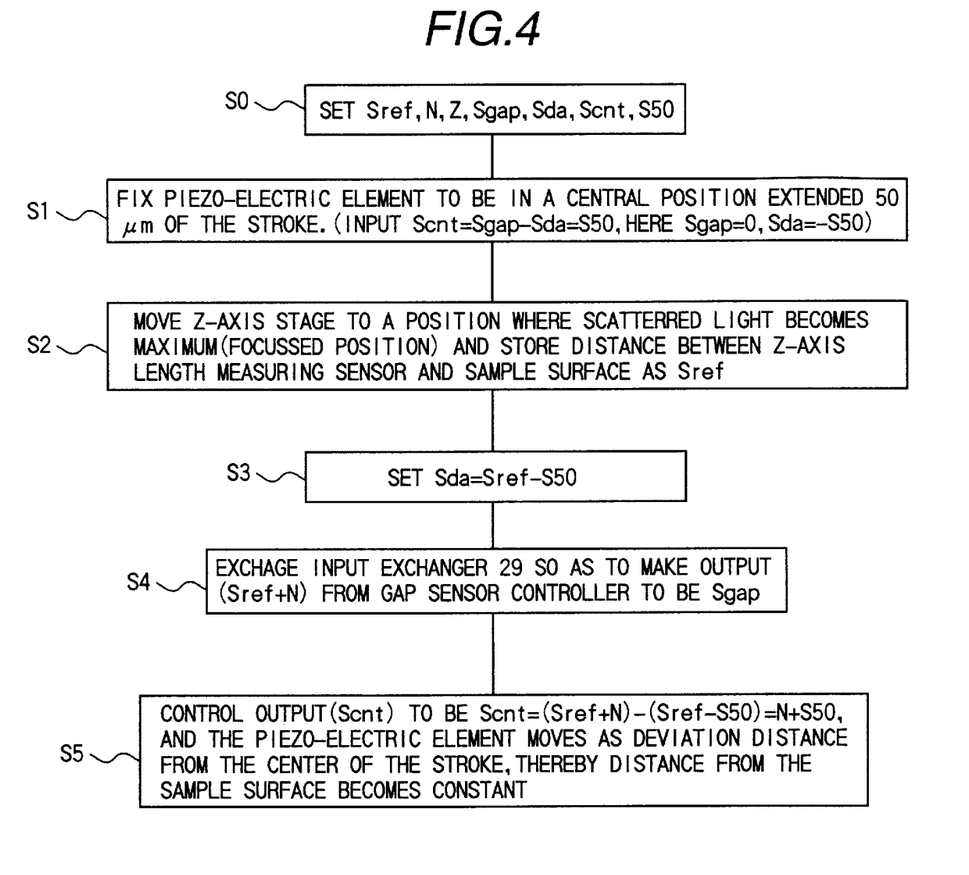
FIG. 4 is a flow chart which shows a control flow for matching focal point.

FIG. 3 is a block diagram representing a control system for focal point matching, and FIG. 4 is a flow chart showing a control flow for the focal point matching.

Signals going from a length measuring sensor controller 24 to piezo electric element controller 20 to 22 are defined as Sgap, and signals going from digital-to-analog converter 27 to the piezo electric element controller 20 to 22 defined as Sda.

Subtracting circuit 30 outputs a result of calculating an equation of Sgap−Sda=Scnt to the piezo electric element controllers 20–22.

As shown in FIG. 4, following signals are set in step $S_0$.
Sref: signal from the length measuring sensor controller 24 at a position where the scattering light intensity becomes maxmum,
N: moving displacement of the wafer or the stage from Sref while measuring the sample,
Z: distance between the wafer and the length measuring sensor probe,
Sgap: signal supplied from the length measuring sensor controller 24 to the piezo electric element controller,
Sda: output signal from D/A converter 27,
Scnt: input signal (Sgap−Sda) to the length measuring sensor controller 24,
$S_{50}$u: signal to move the piezo electric element 50 μm.

Then in step $S_1$, the piezo electric element is fixed to an intermediate position of the stroke.

After, having loaded the sample 15 on the sample stage 19, CPU 26 controls an input exchanging department 29 so as to make the Sgap grounded. That is, Sgap becomes 0.

The CPU 26 gives a signal the digital-to-analog converter 27 so as to be displaced to the center position of the movable range of the piezo electric element 11 to 13, that is, only the amount reduced 50 μm extent as an offset.

The subtracting circuit 30 gives a difference ($S_{50}$) between an earth signal (=0) and a signal of displacement quantity of 50 μm (defined as $S_{50}$) to the first to third piezo electric element controllers 20 to 22.

Thereby, the piezo electric element 11 to 13 fixes the optical system 4, 8 and the objective lens 9 to a position of only 50 μm under the most upper part. Here, this position is in an intermediate position of the stroke, and the direction of the stroke is vertical to the surface of the silicon wafer as the sample.

In a step $S_2$ in the next, the Z axis stage 18 is moved (coarse control) so as to make the scattering light intensity maximum, and output signal of the length measuring sensor controller 24 of this time stored as Sref.

Then, at first, the Z axis stage 18 moves up and down the optical system holder 17 at a position where the scattering light intensity of the first irradiation light 1 or the second irradiation light 5 reflected from the sample surface becomes maxmum.

The movement of the optical system holder 17 is performed by controlling the Z shaft stage controller 23 with the CPU 26.

The position where the scattering light intensity becomes maxmum is previously set to be almost a center position of measurable range of the length measuring sensor 14.

After moving to a Z shaft direction position where the scattering light intensity becomes maximum, the CPU 26 takes in so as to store the signal obtained from the length measuring sensor controller 24 at the position where the scattering light intensity becomes maximum in the analog-to-digital converter 25, and the signal stored in the analog-to-digital converter 25 is defined as Sref.

In step S3 to continue, Sda=Sref−$S_{50}$ is output as the output of the digital-to-analog converter 27.

Then in step $S_4$, the signal from the length measuring sensor controller 24 is controlled to arrive at the subtracting circuit 30 by controlling the input exchanging department 29. According to the above steps, the piezo electric element 11 to 13 become a control condition as shown in step $S_5$. That is, when a quantity of deviation from the signal Sref from the length measuring sensor controller 24 while measuring the sample is defined as N, the output from the length measuring sensor controller 24 becomes Sref+N.

The subtracting circuit 30 outputs Scnt=Sgap−Sda to the first to third piezo electric element controllers 20 to 22, A quantity of the signals, that is, the quantity of displacement of the first to third piezo electric element 11 to 13 becomes 50 μm added a quantity of the distance displacement N obtained while measuring. The piezo electric element 11 to 13 moves up and down by a distance variation of the surface of the sample 15 from an intermediate position of the stroke of the piezo electric element, thereby it becomes possible to keep the distance between the irradiation system 4, 8 and the sample 15, and the distance between the detection system 9 and the sample 15, constant.

$$Scnt=Sgap-Sda=(Sref+N)-(Sref-S_{50})=S_{50}+N \quad (10)$$

The position where the length measuring sensor 14 measures the distance is different is different from that of the irradiation region or the detection region, however, as the CUP 26 lets the sample scaned through the sample stage controller 28 so as to control the linear velocity of the sample stage 19 constant, the time for the scattering body in the sample 15 to move between them becomes always constant. Therefore, delay circuit is provided between the subtracting circuit 30 and the first to third piezo electric element controllers 20 to 22, controlling of the piezo electric element 11 to 13 may be delaied by only the transit time, or the piezo electric element 11 to 13 may be controlled by reading out the stored output of the subtracting circuit 30 after the transit time.

In this way, the piezo electric element 11 to 13 may be controlled actively by measuring the distance before the measuring point reaches the irradiation region, and it becomes possible to do more correct focal point matching.

A measurement of the crystal defect is performed by using a method for matching the focus as stated above, as follows. In the moment when the scattering body passes the irradiation region, a pulse like scattering light is collected by the objective lens 9.

Two wavelength components of the scattering light collected by the objective lens 9, are divided to the first irradiation light and the second irradiation light by using a dichroic mirror, for example, and is detected by separate sensors.

When the output of sensing device exceeds a threshold set up beforehand,

The CPU 26 shown in FIG. 3 reads in r and θ coordinate when the pulse scattering light generating is generated through the stage controller 28, and is stored.

At the same time, the scattering light intensity of the first irradiation light 1 and the second irradiation light 5 are read, so as to be memorized or to be recorded.

From the scattering light intensities $S_1$, $S_2$ detected in this way by the first and second irradiation light in this way, the depth and the size of the defect can be obtained based on the equations (8), (9) stated above.

According to the present invention, in the crystal defect measurement equipment for detecting the scattering light reflected vertically from the scattering body which the light comes in slantingly, the distance with between the irradiation system and the sample, and distance between the detection system and the sample are kept to be constant, and relative position of the irradiation region and the detection region can be kept to be constant, during measuring the sample while the sample is rotated and the center thereof is moved simultaneously, thereby, when total surface of the wafer should be measured, a certain necessary accuracy of the measurement can be attained.

What is claimed is:

1. A crystal defect measurement method for measuring an inner defect of sample, by letting light beams come in slantingly to a surface of the sample being moved, said light beams having two wavelengths and penetration depths thereof to the sample being different, and by detecting scattering lights having said two wavelengths generated from interior of said sample with an detection optical system arranged upward of said surface, said crystal defect measurement method comprising the steps of:

measuring a height of said surface with a distance measurement means of an electrostatic capacitance type arranged to be upstream in a moving direction of the sample from said irradiation optical system and said detection optical system, and controlling a height position of said irradiation optical system and said detection optical system to said sample, so that said irradiation optical system and said detection optical system are disposed at a predetermined position with respect to a measuring point on said sample, when said measuring point on said sample measured by said distance measurement means arrives below said detection optical system.

2. A crystal defect measurement equipment for measuring an inner defect of sample, comprising a sample movement system to let sample move, an irradiation optical system for irradiating light beams slantingly to a surface of the sample being moved, said light beams having two wavelengths and penetration depth thereof to the sample being different, and an detection optical system arranged upward of said surface, wherein an inner defect of said sample is measured by detecting scattering light having two wavelengths from sample interior with said detection optical system, said crystal defect measurement equipment characterized by further comprising a distance measurement system for measuring a surface height of said sample being moved, an optical system movement for moving said irradiation optical system and said detection optical system to a direction that is perpendicularity to said surface, and a control system for controlling said optical system movement system, wherein said control system controls said optical system movement system so as to make a distance between said surface of said sample, and said irradiation optical system and said detection optical system, a predetermined value based on said surface height of said sample measured by said distance measurement system.

3. A crystal defect measurement equipment for measuring an inner defect of sample, as defined in claim 2, comprising a distance measurement device of electrostatic capacitance type in said distance measurement system.

4. A crystal defect measurement equipment for measuring an inner defect of sample, as defined in claim 2, comprising plural distance measurement devices of electrostatic capacitance type in said distance measurement system.

5. A crystal defect measurement equipment for measuring an inner defect of sample, as defined in claim 2, wherein said irradiation optical system and said detection optical system are unified constitutionally, and said optical system movement system moves said unified irradiation optical system and detection optical system with an piezo electric element.

6. A crystal defect measurement equipment for measuring an inner defect of sample, as defined in claim 2, wherein said optical system movement system comprises a piezo electric element for letting said irradiation optical system move, and a piezo electric element for letting said detection optical system move.

7. A crystal defect measurement equipment for measuring an inner defect of sample, comprising a sample movement system to let sample move, an irradiation optical system for irradiating light beams slantingly to a surface of the sample being moved, said light beams having two wavelengths and penetration depth thereof to the sample being different, and an detection optical system arranged upward of said surface, wherein an inner defect of said sample is measured by detecting scattering light having two wavelengths scattered from sample interior with said detection optical system, said crystal defect measurement equipment characterized in that said sample movement system rotates said sample and moves a rotation center of said sample simultaneously so as to make a linear velocity at an irradiation position by said irradiation optical system constant, and further comprising a distance measurement system being located in an upstream of a movement direction of said sample than said irradiation optical system and said detection optical system for measuring a surface height of said sample being moved, a storage system for storing said surface height of said sample measured by said distance measurement system, and an optical system movement system for moving said irradiation optical system and said detection optical system to a direction that is perpendicularity to said surface, and a control system for controlling said optical system movement system, wherein said control system controls said optical system movement system so as to make a distance between said surface of said sample, and said irradiation optical system and said detection optical system, a predetermined value based on said surface height of said sample measured by said distance measurement system.

8. A crystal defect measurement equipment for measuring an inner defect of sample, as defined in claim 7, wherein said control system reads out said surface height of said measurement point stored in said storage system, when the measurement point where said surface height is measured by said distance measurement system arrives at a position just under said detection optical system, and controls said optical system movement system so as to make a distance between said surface of said sample, and said irradiation optical system and said detection optical system, a predetermined value.

9. A crystal defect measurement equipment for measuring an inner defect of sample, as defined in claim 7, comprising a time delay system to delay output of said distance measurement system only a time necessary for the measurement point where the surface height thereof is measured by the distance measurement system to arrive at a position just under the detection optical system in stead of said storage system, wherein said control system controls said optical system movement system so as to make a distance between said surface of said sample, and said irradiation optical system and said detection optical system to be a predetermined value, based on information of the surface height delayed by said time delay system.

10. A crystal defect measurement equipment for measuring an inner defect of sample, as defined in claim 7, comprising other distance measurement system being located in a downstream of said movement direction of said sample than said irradiation optical system and said detection optical system for measuring a surface height of said sample being moved, wherein said control system controls said optical system movement system so as to make a distance between said surface of said sample, and said irradiation optical system and said detection optical system to be a predetermined value, based on information of the surface height obtained by said distance measurement system and said other distance measurement system.

11. A crystal defect measurement equipment for measuring an inner defect of sample, as defined in claim 7, comprising plural distance measurement devices are provided in said distance measurement system, wherein said plural distance measurement instruments are respectively arranged to be vertical to a rotational direction of the sample.

12. A crystal defect measurement equipment for measuring an inner defect of sample, comprising a sample movement system to let sample move, an irradiation optical system for irradiating light beams slantingly from upward of the sample to a surface of the sample being moved by said sample movement system, and an detection optical system arranged upward of said surface for detecting scattering light generated by irradiating said light beams on said sample, said crystal defect measurement equipment further comprising a height detector located in an upstream of a movement direction of said sample than said irradiation optical system and said detection optical system for measuring a surface height of said sample, wherein a movement mechanism for adjusting a height position of said sample and/or said irradiation optical system and said detection optical system so that a distance between said sample and said irradiation optical system and said detection optical system is a predetermined value, based on a height information obtained by said height detector.

* * * * *

UNITED STATES PATENT AND TRADEMARK OFFICE
CERTIFICATE OF CORRECTION

PATENT NO. : 6,108,079
DATED : August 22, 2000
INVENTOR(S) : Muneo Maeshima et al.

It is certified that error appears in the above-identified patent and that said Letters Patent is hereby corrected as shown below:

Column 7,
Line 32, change "5 82 m," to -- 5 µm, --.

Column 8,
Line 54, change "$\sigma\ d^{-6}\gamma^{-4}$" to -- $\sigma \propto d^{-6}\gamma^{-4}$ --.

Column 9,
Line 17, change "$\sigma 2\ d^{-6}$" to -- $\sigma \propto d^{-6}$ --.

Signed and Sealed this

Twenty-ninth Day of January, 2002

Attest:

JAMES E. ROGAN
*Director of the United States Patent and Trademark Office*

*Attesting Officer*